US00PP08587P

United States Patent [19]

Stravers

[11] Patent Number: Plant 8,587

[45] Date of Patent: Feb. 8, 1994

[54] GERBERA PLANT: "TERREINO"

[75] Inventor: Lambertus J. M. Stravers, Kudelstaart, Netherlands

[73] Assignee: Terra Nigra B.V., De Kwakel, Netherlands

[21] Appl. No.: 942,278

[22] Filed: Sep. 9, 1992

[30] Foreign Application Priority Data

Nov. 9, 1989 [NL] Netherlands ..... GRB 1061

[51] Int. Cl.[5] ..... A01H 5/00

[52] U.S. Cl. ..... Plt./68.1

[58] Field of Search ..... Plt. 68.1

*Primary Examiner*—James R. Feyrer
*Assistant Examiner*—Elizabeth C. Kemmerer

[57] ABSTRACT

A new and distinct cultivar of Gerbera plant named 'Terreino', characterized by its semi-double type, a pink ray floret which is a solid pink color throughout, a red-purple disc floret the outermost petaloids of which fade to pink and display white stigmas and brown anthers, pink perianth lobe color and 120 mm overall flower diameter is disclosed.

1 Drawing Sheet

BACKGROUND OF THE INVENTION

The present invention comprises a new and distinct cultivar of *Gerbera Jamesonni,* referred to by the cultivar name 'Terreino'. 'Terreino' was originated from a hybridization program in De Kwakel, The Netherlands in 1985. The female parent was 'Terfame' (reg.nr.7455; Oct. 6, 1986); and the male parent was unnamed seedling 84.359. The female parent 'Terfame' has a yellow color without a dark center, has a single flower, and has a shorter vase-life. 'Terfame' has been available outside Terra Nigra, but 'Terfame' has not been patented in the USA. The male parent 84.359 has a color similar to 'Terreino' but a smaller flower-diameter and a shorter vase-life. 84.359 had not been available outside Terra Nigra. The new cultivar was selected by me from the progeny of the stated parentage on or about November 1985. The first asexual reproduction of 'Terreino' was accomplished when vegetative cuttings were taken on April 1986 in De Kwakel. The new cultivar is presently being propagated by cuttings and tissue culture. Horticultural examination of selected units initiated November 1986 has demonstrated that the combination of characteristics as herein disclosed for 'Terreino' are firmly fixed and are retained through successive generations of asexual reproduction. The following observations, measurements and comparisons describe plants grown in De Kwakel, The Netherlands, under greenhouse conditions which closely approximate those generally used in commercial practice. The following traits have been repeatedly observed and are determined to be basic characteristics of 'Terreino', which in combination distinguish this Gerbera from its parents and all other varieties of which I am aware:

1. Type: Semi-double.
2. Color of ray floret: Pink.
3. Color of disc floret: Distinctive red-purple.
4. Color of perianth lobe: Pink.
5. Diameter of flower head: Large 120 mm.

Of the many commercial cultivars known to me, there is no cultivar similar in comparision to 'Terreino'.

BRIEF DESCRIPTION OF THE FIGURE OF THE DRAWING

The accompanying photographic drawing shows typical inflorescence and foliage characteristics nearly true as possible. In the following description, color references are made to The Royal Horticultural Society Color Chart (R.H.S.). The color values were determined at 11.30 a.m. on Oct. 27, 1989 under natural light at De Kwakel.

BOTANICAL DESCRIPTION OF THE PLANT

Botanical: *Gerbera jamessonii* cv Terreino.

1. INFLORESCENCE

A. Capitulum:
- *Form.*—Flat shaped.
- *Type.*—Semi-double.
- *Diameter across face.*—120 mm.

B. Corolla of ray florets:
- *Color (general tonality from a distance of 3 meters).*—Pink.
- *Color (topside).*—RHS 36C.
- *Color (bottom).*—RHS 19D.

C. Corolla of disc florets:
- *Color (mature)* —Purple RHS 187A.
- *Color (immature).*—Purple RHS 187A.

D. Reproductive organs:
- *Stigma.*—White RHS 155B.
- *Anthers.*—Brown RHS 183C.
- *Pappus.*—Dark yellow RHS 14C.

2. PLANT

A. General appearance:
- *Height.*—40 cm.

B. Foliage:
- *Color (abaxial).*—RHS 137A.
- *Color (adaxial).*—RHS 138B.
- Shape.—The angle of apex: Weakly Obtuse. The shape of apex: Pointed. The margin of lobes: Sinuate.

C. Disease resistance: No special disease resistance.

3. OTHER CHARACTERISTICS

The following traits have been repeatedly observed and are determined to be basic characteristics of 'Terreino', which in combination distinguish this Gerbera as a new and distinct cultivar.

Leaf blade:

*Length.*—Medium (52 cm).

*Width.*—Medium (23 cm).

*Thickness.*—Medium.

*Blistering.*—Weak.

*Pubescence.*—On upper side (midrib excluded) of the leaf blade is medium.

*Depth of cuts or incisions in leaf.*—Basal part: Medium. Central part: Medium. Distal part: Shallow.

*Color.*—Upper side of the leaf blade is medium green (RHS 137A).

*Glossiness on upper side.*—Medium.

*Angle of apex.*—Weakly obtuse.

*Shape of apex.*—Pointed.

*Margin of lobes.*—Sinuate.

*Extensions of margin.*—Small.

*Petiole length.*—Medium.

*Petiole anthocyanin coloration.*—Medium.

Peduncle:

*Length.*—Medium (65 cm).

*Cross section.*—Round.

*Tendency to fasciation.*—Absent.

*Thickness.*—Medium.

*Strength.*—Strong.

*Pubescence.*—Medium.

*Color.*—Medium green.

*Anthocyanin coloration.*—At base: Medium. At top: Absent.

*Involucral bracts.*—Absent.

Flower head:

*Type.*—Semi-double.

*Diameter.*—Medium/Large (approx. 120 mm).

*Involucre.*—Height: Medium (16 mm). Diameter: Large. Number of bracts: Medium (37). Longitudinal axis of bracts of inner rows: Reflexing. Anthocyanin: Present. Pubescence: Medium.

*Ray florets.*—Number: Medium (41). Shape: Narrow elliptic. Longitudinal axis outer row: Reflexing. Longitudinal axis inner row: Straight.

*Outer ray florets.*—Cross section: Convex. Length: Medium (43 mm). Width: Broad. Longitudinal folding: Medium. Angle of apex: Acute. Shape of apex: Pointed. Incisions of apex: Present. Number: One. Depth: Shallow. Length of free petals: Short. Color distribution on inner side: Uniform. Edge of different color: Absent. Striation: Absent. Claw spot: Present.

Disc florets:

*Diameter.*—Medium.

*Main color perianth lobes.*—Pink for both female and male flowers (RHS 55C).

Reproductive parts:

*Stigma.*—Main color white (RHS 155B).

*Anthers.*—Main color purple (RHS 183C). Color of top relative to other parts is darker. Longitudinal striping: Present.

*Pappus.*—Main color yellow (RHS 14C). Color of top relative to other parts is darker. Orientation: Level of top relative to closed disc florets is above.

*Fertility.*—Very good (about 250 pollen). The plant will form seed easily.

I claim:

1. A new and distinct cultivar of Gerbera plant named 'Terreino', as illustrated and described, characterized by its semi-double type, a pink ray floret which is a solid pink color throughout, a red-purple disc floret the outermost petaloids of which fade to pink and display white stigmas and brown anthers, pink perianth lobe color and 120 mm overall flower diameter.

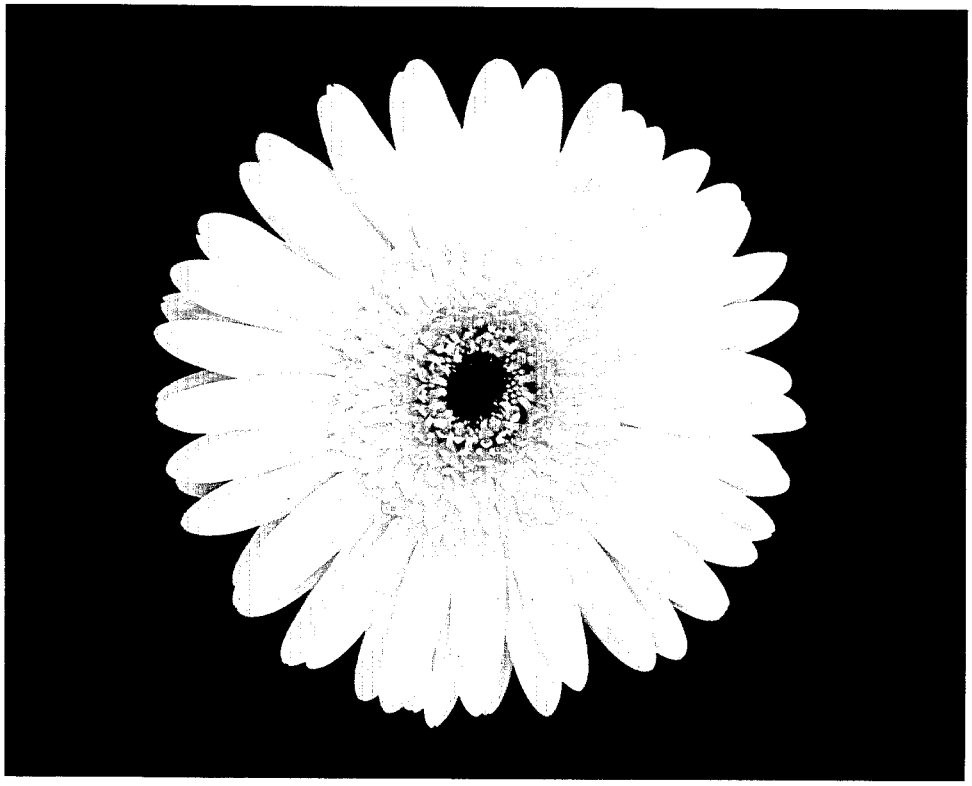

* * * * *